(12) United States Patent
Bertet et al.

(10) Patent No.: US 10,422,838 B2
(45) Date of Patent: Sep. 24, 2019

(54) METHOD AND DEVICE FOR VERY HIGH SENSITIVITY ELECTRON SPIN RESONANCE SPECTROSCOPY

(71) Applicant: Commissariat A L'Energie Atomique Et Aux Energies Alternatives, Paris (FR)

(72) Inventors: Patrice Bertet, Paris (FR); Klaus Moelmer, Aarhus N (DK)

(73) Assignee: Commissariat A L'Energie Atomique Et Aux Energies Alternatives, Paris (FR)

( * ) Notice: Subject to any disclaimer, the term of this patent is extended or adjusted under 35 U.S.C. 154(b) by 217 days.

(21) Appl. No.: 15/554,493

(22) PCT Filed: Mar. 2, 2016

(86) PCT No.: PCT/FR2016/050467
§ 371 (c)(1),
(2) Date: Aug. 30, 2017

(87) PCT Pub. No.: WO2016/139419
PCT Pub. Date: Sep. 9, 2016

(65) Prior Publication Data
US 2018/0045795 A1    Feb. 15, 2018

(30) Foreign Application Priority Data
Mar. 3, 2015 (FR) ...................................... 15 51786

(51) Int. Cl.
*G01R 33/34* (2006.01)
*G01N 24/10* (2006.01)
(Continued)

(52) U.S. Cl.
CPC ....... *G01R 33/34015* (2013.01); *G01N 24/10* (2013.01); *G01R 33/3614* (2013.01); *G01R 33/60* (2013.01)

(58) Field of Classification Search
CPC ................ G01R 33/60; G01R 33/3614; G01R 33/34015; G01N 24/10
See application file for complete search history.

(56) References Cited

U.S. PATENT DOCUMENTS 8,207,503 B2 * 6/2012 Goulon ................... G01T 1/241
250/370.01
8,593,141 B1 * 11/2013 Radparvar ........... G01R 33/323
324/248
(Continued)

OTHER PUBLICATIONS

Artzi et al.; "Induction-detection electron spin resonance with spin sensitivity of a few tens of spins"; Applied Physics Letters; 2015; pp. 1-5; vol. 106.
(Continued)

*Primary Examiner* — Dixomara Vargas
(74) *Attorney, Agent, or Firm* — The Webb Law Firm

(57) ABSTRACT

A device for detecting and characterising electron spins in a sample includes an electromagnetic microresonator, having a resonant frequency cor in the microwave range and a quality factor Q and into which the sample is inserted; a device for creating a magnetic field B0 in the sample for bringing a spin transition frequency cos into resonance with the resonant frequency cor, such that cos=γB0, where γ is a gyromagnetic factor of the spins; a spin detection device receiving signals from the electromagnetic microresonator associated with the sample and including at least one low-noise amplifier operating at a temperature of between 1 and 10 K and a series of amplifiers and a demodulator operating at ambient temperature.

20 Claims, 2 Drawing Sheets

(51) Int. Cl.
*G01R 33/60* (2006.01)
*G01R 33/36* (2006.01)

(56) References Cited

U.S. PATENT DOCUMENTS

| | | | | |
|---|---|---|---|---|
| 8,618,799 | B1* | 12/2013 | Radparvar | G01R 33/323 |
| | | | | 324/248 |
| 9,170,311 | B2* | 10/2015 | Apostolos | G01N 24/084 |
| 9,261,573 | B1* | 2/2016 | Radparvar | G01R 33/323 |
| 9,331,772 | B2* | 5/2016 | Harris, III | H04B 7/0602 |
| 9,618,591 | B1* | 4/2017 | Radparvar | G01R 33/323 |
| 10,295,636 | B2* | 5/2019 | Song | G01N 24/081 |
| 2010/0065748 | A1* | 3/2010 | Goulon | G01T 1/24 |
| | | | | 250/370.12 |
| 2012/0215092 | A1* | 8/2012 | Harris, III | H04B 7/0602 |
| | | | | 600/410 |
| 2014/0113828 | A1* | 4/2014 | Gilbert | G01R 33/0354 |
| | | | | 505/100 |
| 2018/0092557 | A1* | 4/2018 | Bickford | A61B 5/0059 |
| 2018/0284175 | A1* | 10/2018 | Bickford | A61B 5/04001 |

OTHER PUBLICATIONS

Bachar et al.; "Nonlinear induction detection of electron spin resonance"; Applied Physics Letters; 2012; pp. 1-4; vol. 101.
Bergeal et al.; "Phase-preserving amplification near the quantum limit with a Josephson ring modulator"; Nature Letters; 2010; pp. 64-69; vol. 465.
Castellanos-Beltran et al.; "Widely tunable parametric amplifier based on a superconducting quantum interference device array resonator"; Applied Physics Letters; 2007; pp. 1-3; vol. 91.
Kubo et al.; "Electron spin resonance detected by a superconducting qubit"; Physical Review B; 2012; pp. 1-6; vol. 86.
Malissa et al.; "Superconducting coplanar waveguide resonators for low temperature pulsed electron spin resonance spectroscopy"; Review of Scientific Instruments; 2013; pp. 1-5; vol. 84.
Sigillito et al.; "Fast, low-power manipulation of spin ensembles in superconducting microresonators"; Applied Physics Letters; 2014; pp. 1-4; vol. 104.
Twig et al.; "Sensitive surface loop-gap microresonators for electron spin resonance"; Review of Scientific Instruments; 2010; pp. 1-11; vol. 81.

* cited by examiner

METHOD AND DEVICE FOR VERY HIGH SENSITIVITY ELECTRON SPIN RESONANCE SPECTROSCOPY

CROSS-REFERENCE TO RELATED APPLICATIONS

This application is the U.S. national phase of International Application No. PCT/FR2016/050467 filed Mar. 2, 2013, and claims priority to French Patent Application No. 1551786 filed Mar. 3, 2015, the disclosures of which are hereby incorporated in their entirety by reference.

BACKGROUND OF THE INVENTION

Field of the Invention

The present invention relates to a device and method that are intended to be used to perform electron-spin-resonance (ESR) spectroscopy with a greater sensitivity than in the prior art.

ESR spectroscopy in particular has applications in structural biology, solid-state physics and archaeology.

Prior Art

Current spectrometers have a sensitivity that typically allows them to detect 109 spins in one second of integration time.

The purpose of an ESR spectrometer 10 is to detect and characterize electron spins in a given sample 1. To do this, the sample 1 is inserted into an electromagnetic resonator 2 having a resonant frequency ωr in the microwave domain (typically from 5 to 10 GHz) and a quality factor Q (see FIG. 1).

A magnetic field B0 is applied to the sample 1 in the direction of the arrow 3 by a coil or any other type of device (not shown) for creating a magnetic field, in order to bring the transition frequency of the spins (given by ωs=γB0, γ being the gyromagnetic ratio of the spins) into resonance with the resonant frequency ωr.

This magnetic resonance is detected by virtue of a microwave signal that is injected into the cavity at the frequency ωr by a device 4 and collected, on exiting the sample 1, by a device 5, in order to be amplified by an amplifying device 6.

The transmission T of this signal is decreased when ωs=ωr, because the spins then absorb this microwave signal, this manifesting itself in the appearance of resonant dips in the curve T(B0). The frequency and width of the dips, and their relative amplitude, allow a number of pieces of information on the sample 1 to be extracted.

This spectrometer operating mode is called continuous-wave EPR spectroscopy.

Another widely used operating mode (referred to as "pulsed EPR") that implements a device such as that in FIG. 1 consists in using sequences of brief microwave pulses that cause the spin to rotate by a well-defined Rabi angle.

One of the most used sequences is called the spin-echo sequence. It consists in applying a first pulse that causes the spins to rotate by an angle of π/2, followed, after a time τ, by a second pulse that causes a rotation of angle π. Spins meeting the condition of resonance ωs=ωr then emit an echo signal at the time 2τ.

The dependence of the amplitude of this echo signal on certain parameters (magnetic field, angle, time τ between the pulses, etc.) contains all the information able to be extracted from the sample.

Detection of the spin-echo signal is therefore essential and is the keystone of electron-paramagnetic-resonance spectroscopy.

The maximum power P transmitted during a spin echo to the cable connecting the resonator 1 to the detection chain 6 is given by a simple formula: $P = \hbar \omega r N^2 g^2/\kappa$, N being the number of spins contained in the sample, g being the "coupling constant" of a spin to the microwave field of the cavity, and $\kappa = \omega r/Q$ the damping ratio of the field in the microwave resonator.

The duration of the echo pulse depends on the sample, but is given approximately by the "free-induction time" $T_2^*$.

The sensitivity of the spectrometer may then be quantified by the minimum number of spins Nmin detectable with a signal-to-noise ratio of 1 during a spin echo.

This number clearly depends on the amount of noise added by the first amplifier of the microwave detection chain 6, which is characterized by its noise temperature $T_N$. The degradation of the signal-to-noise ratio during the amplification is given by the number of noise photons added by the amplifier, which is given by $n = 1/(e^{\hbar \omega r / \kappa T_N} - 1)$.

Conventional microwave amplifiers all operate in the limit where $\kappa T_N \gg \hbar \omega r$ and hence $n \approx \kappa T_N / \hbar \omega r$.

The minimum number of spins detectable by the spectrometer in one spin echo is then calculated by setting the number of photons emitted by the spins during an echo $(T_2^* P/\hbar \omega r)$ equal to the number of noise photons emitted during $T_2^*$ in a passband $1/T_2^*$ (i.e. n), this implying that $$N_{min} \approx \coth\left(\frac{\hbar \omega r}{2kT}\right)\frac{1}{g}\sqrt{\frac{n\kappa}{T_2^*}}$$

(the coth first term being due to the equilibrium polarization of the spins at the temperature T).

In a conventional spectrometer, the resonator 2 is a metal box that contains the sample 1, and the microwave field inside the resonator 2 occupies a volume of about $\lambda^3$, λ being the wavelength at the frequency ωr. This results in a typical coupling constant of g=2π×5 mHz. The amplifier 6 at room temperature adds about $n = 10^3$ noise photons. The quality factor is typically 2000. The polarization factor of the spins at room temperature is $$\coth\left(\frac{\hbar \omega r}{2kT}\right) \approx 10^3.$$

This leads to a sensitivity of $N_{min} \approx 10^{13}$ detectable spins in one spin echo for a conventional spectrometer at room temperature.

Recently, new types of spectrometers have been developed, the spectrometers being based on microresonators 102. It is a question of microwave resonators fabricated from thin metal films (see FIG. 2).

The volume of the mode may then be much smaller than $\lambda^3$ and hence the coupling constant may be much higher, reaching g=2π×1 at 20 Hz. Microresonators 102 have been produced with what is called a "loop-gap" geometry, with thin films made of normal metals (see for example the article by Y. Twig, E. Suhovoy, A. Blank, Rev. Sci. Inst. 81, 104703 (2010)).

Microresonators 102 have also been produced in a coplanar waveguide geometry (see the example of FIG. 2) in which the coplanar waveguide is made of superconductive metal, as for example described in the article by H. Malissa, D. I. Schuster, A. M. Tyryshkin, A. A. Houck, S. A. Lyon, Rev. of Sci. Instr. 84, 025116 (2013).

Working at 4 K in order to increase spin polarization, and moreover using better amplifiers cooled to 4 K, for which as few as n=10 to 20 noise photons are obtained, sensitivity has been increased to a record value of $N_{min} \approx 10^7$ spins in one spin echo, which is the highest sensitivity that has been published in the literature to date (see the article by A. J. Sigillito et al., Appl. Phys. Lett. 104, 222407 (2014)). It would however be desirable to be able to further increase such a sensitivity.

OBJECTIVE AND BRIEF DESCRIPTION OF THE INVENTION

An objective of the invention is to provide a method and device allowing up to thirteen orders of magnitude to be gained with respect to conventional ESR spectrometers, and up to seven orders of magnitude to be gained with respect to the prior art, thereby allowing a single spin to be detected in about one second of measurement.

The applications opened up by the invention include ESR spectroscopy of a single protein, of a single biological cell, and the production of a solid-state, spin-based quantum computer.

These aims are achieved by virtue of a very-high-sensitivity spin-resonance spectroscopy device for detecting and characterizing electron spins in a given sample, comprising an electromagnetic microresonator having a resonant frequency $\omega r$ in the microwave domain and a quality factor Q and into which the sample is inserted, a device for creating a magnetic field B0 in the sample in order to bring into resonance with the resonant frequency $\omega r$ a transition frequency $\omega s$ of the spins, such that $\omega s = \gamma B0$, where $\gamma$ is a gyromagnetic ratio of the spins; and a spin-detecting device receiving signals from the electromagnetic microresonator with which the sample is associated and comprising at least one low-noise amplifier operating at a temperature between 1 and 10 K, and a series of amplifiers and a demodulator operating at room temperature, characterized in that the electromagnetic microresonator is made of superconductive metal and is produced on the nanoscale in that it comprises an active zone consisting of an essentially parallelepipedal constriction with a thickness comprised between 8 and 30 nm, a width comprised between 10 and 500 nm and a length comprised between 100 and 5000 nm.

The microresonator may preferably be made of niobium, aluminum, NbN, NbTiN or TiN.

According to one particular embodiment, the device comprises a Josephson parametric amplifier that is placed upstream of the low-noise amplifier and that operates at temperatures T respecting $T \leq \hbar \omega r / \kappa_B$, where $\hbar$ is the reduced Planck's constant and $\kappa_B$ is Boltzmann's constant (the value of which is $\kappa_B = 1.38$ J/K = $1.38 \times 10^{-23}$ m$^2$kgs$^{-2}$K$^{-1}$).

If the working frequency is about $\omega r / 2\pi = 5$ to 10 GHz, a suitable working temperature will therefore be between 10 and 200 mK.

If the working frequency is higher $\omega r / 2\pi = 20$ to 40 GHz, it will be possible to work at a temperature of about 1 to 3 K, which may be reached without using dilution cryogenics.

In this case, according to one advantageous embodiment, the device furthermore comprises an additional Josephson parametric amplifier operating at temperatures T respecting $T \leq \hbar \omega r / \kappa_B$, and placed such that its output is connected to the input of the microresonator in order to produce a "squeezed vacuum" i.e. a quantum state of the electromagnetic field in which the noise in one of the two quadratures is decreased with respect to the vacuum quantum noise.

The spin-detecting device may be a continuous-wave device and then comprises a device for injecting a microwave signal at the frequency $\omega r$ into the electromagnetic microresonator.

According to one possible alternative, the spin-detecting device is a pulsed-wave device and comprises a device for injecting sequences of brief pulses of microwave frequency equal to the frequency $\omega r$ into the electromagnetic microresonator in order to cause the spin to rotate by a well-defined Rabi angle.

Yet another subject of the invention is a very-high-sensitivity spin-resonance spectroscopy method for detecting and characterizing electron spins in a given sample, comprising a step of producing an electromagnetic microresonator having a resonant frequency $\omega r$ in the microwave domain and a quality factor Q and with which the sample is associated; a step of creating a magnetic field B0 in the sample in order to bring into resonance with the resonant frequency $\omega r$ a transition frequency $\omega s$ of the spins, such that $\omega s = \gamma B0$, where $\gamma$ is a gyromagnetic ratio of the spins; and a spin-detecting step in which signals are received from the electromagnetic microresonator with which the sample is associated via at least one low-noise amplifier operating at a temperature comprised between 1 and 10 K, and a series of amplifiers and a demodulator operating at room temperature, characterized in that in the step of producing the electromagnetic microresonator an electromagnetic microresonator made of superconductive metal is chosen, which microresonator is produced on the nanoscale in that it comprises an active zone consisting of an essentially parallelepipedal constriction the dimensions of which are: a thickness of 8 to 30 nm, a width of 10 to 500 nm, and a length comprised between 100 and 5000 nm.

According to one particular embodiment, in the spin-detecting step, a Josephson parametric amplifier is placed upstream of the low-noise amplifier, said Josephson parametric amplifier operating at temperatures T respecting $T \leq \hbar \omega r / \kappa_B$ where $\hbar$ is the reduced Planck's constant and $\kappa_B$ is Boltzmann's constant (the value of which is $\kappa_B = 1.38$ J/K = $1.38 \times 10^{-23}$ m$^2$kgs$^{-2}$K$^{-1}$).

If the working frequency is about $\omega r / 2\pi = 5$ to 10 GHz, a suitable working temperature will therefore be between 10 and 200 mK.

If the working frequency is higher $\omega r / 2\pi = 20$ to 40 GHz, it will be possible to work at a temperature of about 1 to 3 K, which may be reached without using dilution cryogenics.

In the case where a Josephson parametric amplifier is placed upstream of the low-noise amplifier, according to one advantageous embodiment, in the step of producing an electromagnetic microresonator, an additional Josephson parametric amplifier operating at temperatures T respecting $T \leq \hbar \omega r / \kappa_B$ is placed such that its output is connected to the input of the microresonator in order to produce a "squeezed vacuum" i.e. a quantum state of the electromagnetic field in which the noise in one of the two quadratures is decreased with respect to the vacuum quantum noise.

According to the present invention, a plurality of features each contribute to improving the sensitivity of an ESR spectrometer while preserving the basic principle thereof.

With all of the innovations proposed here, the sensitivity of an ESR spectrometer may reach a minimum number of spins detected in one echo $N_{min} \approx 1$, i.e. an improvement of three orders of magnitude with respect to a conventional spectrometer and of seven orders of magnitude with respect to the best value published to date, corresponding to a measurement time that is $10^{26}$ and $10^{14}$ times shorter, respectively.

BRIEF DESCRIPTION OF THE DRAWINGS

Other features and advantages of the invention will become apparent from the following description of particular embodiments, which are given by way of nonlimiting example with reference to the appended drawings, in which.

DETAILED DESCRIPTION OF PARTICULAR EMBODIMENTS OF THE INVENTION

Figures 3, 3A:
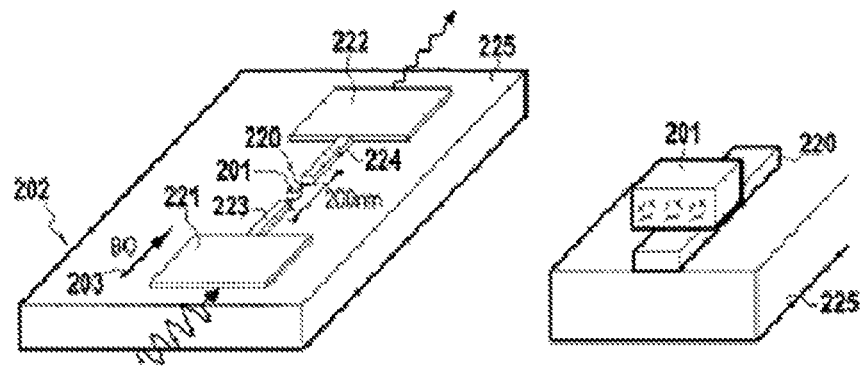
FIG. 3 is a schematic perspective view of a nanoresonator for ESR spectroscopy according to one aspect of the invention.
FIG. 3A is an enlarged view of one portion of the nanoresonator of FIG. 3 showing a constriction receiving a nanoscale sample.

According to a first aspect of the invention, which is shown in FIG. 3, a nanoscale microresonator 202 is employed in an ESR spectrometer.

It is a question, within the inductive portion of a microresonator (for example the microresonator 202 of coplanar geometry shown in FIG. 3), of introducing a small zone 220 in which the dimensions of the resonator become much smaller, typically between 10 and 500 nm (see FIGS. 3 and 3A). Such a constriction 220 may be produced using standard e-beam lithography techniques. Thus, an "active zone" typically of $(100\ nm)^3$ size is obtained within which the spins present will be coupled with a coupling constant that may reach from 1 to 10 kHz, about two orders of magnitude higher than has been achieved up to now.

Figure 1:
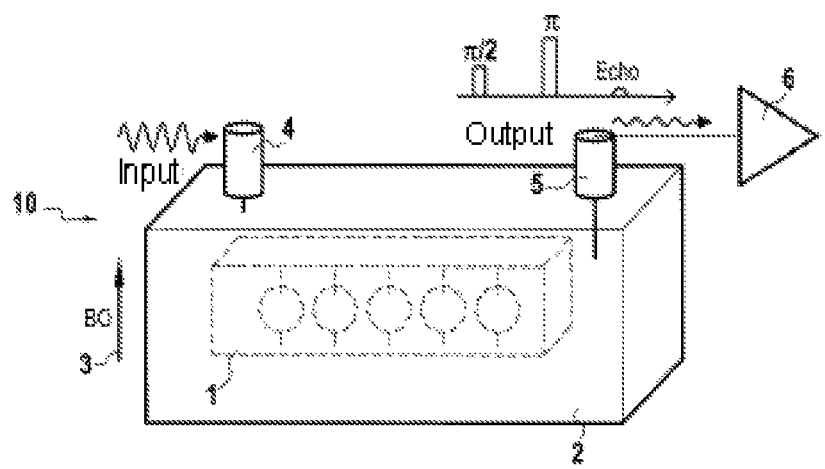
FIG. 1 is a schematic showing the basic structure of an ESR spectrometer.
Figure 2:
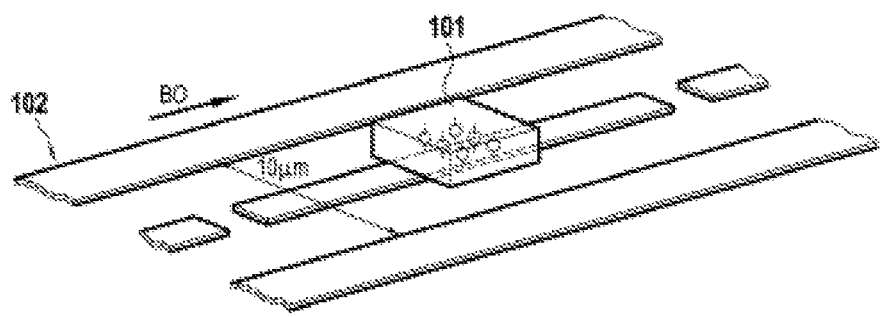
FIG. 2 is a schematic perspective view showing an example of a coplanar-microresonator-based ESR spectrometer.

FIG. 3 shows a substrate 225 on which plate-shaped metal layers 221 and 222 have been placed, these corresponding to the capacitive portion of the resonator of the ESR spectrometer of FIG. 1, which also allows the coupling to the measuring waveguides (not shown). The exact geometry of this capacitive portion may be adapted with respect to that indicated in the schematic, for example an interdigitated capacitor is usable. The metal layers 221 and 222 are aligned in a direction 203 corresponding to the direction of the applied magnetic field B0. The metal layers 221 and 222 are connected together by narrower conductive tracks 223, 224 that are aligned with each other in the direction 203 and joined by an even narrower portion forming the constriction 220 on which a sample 201 to be analyzed is placed (see FIGS. 3 and 3A).

The parallelepipedal-shaped constriction 220 may for example have a cross section of 20 nm×20 nm and a length of 200 nm.

More generally, the essentially parallelepipedal constriction 220 has a thickness from 8 to 30 nm, a width from 10 to 500 nm, and a length comprised between 100 and 5000 nm.

More particularly, the dimensions of the constriction 220 and those of the sample 201 are adapted to be mutually compatible.

In particular, this type of nanoresonator 202 is very suitable for measuring samples 201 of ~100 nm typical size, such as biological samples, with which the amount of available material is very small.

The resonator 202 must imperatively be fabricated from superconductive metal (for example niobium or NbN or NbTiN below 5 K, aluminum below 200 mK, or indeed TiN below 2 K) so that its quality factor Q is high enough for an effective detection (Q preferably being chosen between $10^3$ and $10^5$).

The other elements of the ESR spectrometer may be such as those described above.

In particular, the electromagnetic microresonator 202 having a resonant frequency ωr in the microwave domain and a quality factor Q and into which the sample 201 is inserted and a device for creating a magnetic field B0 in the sample 201 in order to bring into resonance with the resonant frequency ωr a transition frequency ωs of the spins, such that ωs=γB0, where γ is a gyromagnetic ratio of the spins, the ESR spectrometer according to the invention comprises a spin-detecting device receiving signals from the electromagnetic microresonator 202 and from the sample 201.

Figure 4:
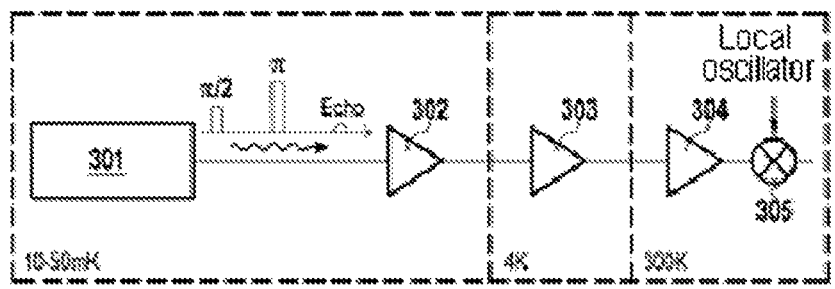
FIG. 4 is a schematic of a Josephson-parametric-amplifier-based ESR spectrometer according to a second aspect of the invention.

The spin-detecting device comprises at least one low-noise amplifier 303 operating at a temperature comprised between 1 and 10 K, and a series of amplifiers 304 and a demodulator 305 operating at room temperature, as shown in FIG. 4.

A second aspect of the invention, which also contributes to increasing detection sensitivity, and that is therefore advantageously implemented with the nanoresonator 202 described above with reference to FIG. 3 in order to increase the sensitivity of the latter, but that may also be implemented independently of the nanoresonator 202 described above, i.e. could be implemented with a conventional microresonator or resonator without a constriction and capable of receiving a sample of arbitrary size, will now be described with reference to FIG. 4.

According to this other aspect of the invention, a Josephson parametric amplifier is used. Josephson parametric amplifiers are a type of microwave amplifier recently developed for quantum computer applications and the major advantage of which is to have the best possible noise performance since they reach the limit of what is achievable in quantum physics, i.e.: n= 0.5 to 1.

Josephson parametric amplifiers (JPAs) are based on superconductor circuits containing Josephson junctions. They typically operate at temperatures T such that $T \leq \hbar \omega r/\kappa_B$ where $\hbar$ is the reduced Planck's constant and $\kappa_B$ is Boltzmann's constant (the value of which is $\kappa_B$=1.38 J/K=1.38× $10^{-23}$ $m^2 kgs^{-2} K^{-1}$).

This corresponds to temperatures from 10 to 200 mK for frequencies from 5 to 10 GHz, and to temperatures from 1 to 3 K for frequencies from 20 to 40 GHz. They have been used in various experiments, but not for high-sensitivity magnetic-resonance measurements.

The reader may in particular refer to the article by M. A. Castellanos-Beltran, K. W. Lehnert, Appl. Phys. Lett. 91, 083509 (2007) and to the article by N. Bergeal et al., Nature 465, 64 (2010).

According to the invention, it has been found that, for high-sensitivity magnetic-resonance measurements, it is advantageous to use a JPA in the "degenerate" regime, in which regime amplification of just one quadrature with no addition of noise by the amplifier is achieved by setting up the amplifier so that only the quadrature in which the spin echo is emitted is amplified. In this regime, the only noise limiting the measurement sensitivity is the vacuum quantum noise, this corresponding to n=0.5.

If reference is made to FIG. 4, it may be seen that, using an assembly 301 comprising a resonator and a sample, which may advantageously consist of a resonator 202 and a sample 201 such as described above with reference to FIGS. 3 and 3A to obtain a maximum sensitivity, but that could also be produced in the conventional way without the constriction 220 of the resonator 202, the signals induced in the resonator subjected to a magnetic field B0 as indicated above are applied to a Josephson parametric amplifier 302 (JPA amplifier) placed, just like the assembly 301, in an environment the temperature of which is that adapted to the amplifier 302 as indicated above.

The output of the JPA amplifier 302 is connected to the input of a low-noise amplifier 303, itself placed in an environment at a temperature between 1 and 10 K. The output of the low-noise amplifier 303 is connected to the input of a series of amplifiers 304, which series is associated with a demodulator 305 implementing a local oscillator. All of the series of amplifiers 304 and the demodulator 305 are at room temperature, for example about 300 K.

Figure 5:
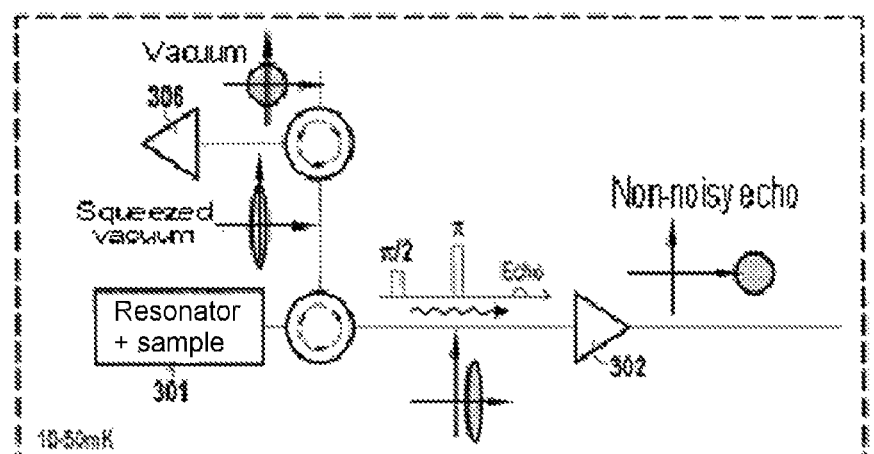
FIG. 5 is a schematic of one particular embodiment that is an improvement on the ESR spectrometer of FIG. 4 with regard to producing a non-noisy echo.

FIG. 5 illustrates an improvement to the embodiment of FIG. 4.

In the embodiment in FIG. 5, a device generating a squeezed vacuum is used in order to further increase, by a factor of possibly of as much as one order of magnitude, the sensitivity of the spectrometer. Squeezed vacuum is a quantum state of the electromagnetic field in which the noise on one of the two quadratures is decreased by a factor S with respect to the vacuum quantum noise, i.e. the number of noise photons added becomes n= 0.5/S. In practice, it is possible to achieve S= 10 to 100. The squeezed quadrature is chosen so that it corresponds to that on which the spin echo is emitted. The sensitivity of the spectrometer is then further increased by a factor $\sqrt{S}$, i.e. potentially by an order of magnitude more.

The squeezed vacuum is generated by an additional degenerate-mode JPA amplifier 306 placed such that its output is connected to the input of the assembly 301 comprising the resonator and the sample in the spectrometer (see FIG. 5). This improvement is useful in the case where the echo signal is then amplified by a JPA amplifier 302 at the quantum limit, as indicated above with reference to FIG. 4. The non-noisy echo output from the JPA amplifier 302 at the quantum limit is then amplified by the amplifiers 303 and 304 and demodulated by the demodulator 305 as illustrated in FIG. 4 and these elements have not been shown again in FIG. 5.

By combining the three embodiments of FIGS. 3 to 5, $N_{min}$=0.5 is achieved (for g=2π×5 kHz, T=10 mK, S=100, Q=$10^5$). This means that it becomes possible to perform EPR-spectroscopy measurements on any electron spin at the scale of a single spin.

The invention thus aims to very significantly increase the sensitivity of an electron-paramagnetic-resonance (EPR) (a.k.a. electron-spin-resonance (ESR)) detection chain that allows the magnetic moment of electron spins of a sample of material to be tested to be measured.

Sensitivity amounts to a quantification of the number of detected electron spins, and is measured either in spins/√Hz ($10^9$ spins/√Hz at 300 K for commercially available devices) or in number of electron spins detected in a single echo (typically $10^{13}$ spins at 300 K with commercially available devices). It will be noted that experimental apparatuses measure this sensitivity in number of spins per echo, these two quantities being related by the repetition rate, which itself is set by the energy relaxation time $T_1$ of the spins, which may depend on the type of spin in question. The best sensitivity that has been achieved in the laboratory is N1echo≈5×$10^7$ spins at 1 or 2 K.

In practice, this is achieved via superconductive planar resonators, in which a waveguide confines a planar resonator so as to form a resonator of very high quality coefficient (Q≈$10^4$). The output of the planar resonator is conventionally applied directly to a low-noise amplifier cooled to a temperature comprised between 1 and 10 K, such as the amplifier 303 of FIG. 4. The invention, in the embodiment of FIG. 4, consists in introducing, between on the one hand the assembly 301 formed by the resonator and the sample and on the other hand the amplifier 303, a device issued from quantum physics, namely the JPA amplifier 302, which is an "amplifier at the quantum limit". This "amplifier at the quantum limit" has an extremely low noise level, and improves the signal-to-noise ratio by about 10. The invention encompasses any possible type of superconductive resonator and therefore, a priori, superconductive resonators of any shape, although a preferred embodiment is that described with reference to FIGS. 3 and 3A.

In the embodiment of FIG. 5, on the side opposite the output of the planar resonator, a second "amplifier at the quantum limit" (JPA amplifier 306 of FIG. 5) is added, the operation of which is slightly different but that again in the end also leads to a decrease in noise by generating a "squeezed vacuum" state at its output.

Lastly, the quality coefficient of the cavity is also a key point.

The core of the invention consists of a planar superconductive microwave resonator intended to measure a set of spins coupled to the oscillating magnetic field of the resonator. The resonator may be fabricated from a material allowing magnetic fields of up to 1 Tesla to be applied while preserving a high quality factor (between $10^4$ and $10^5$).

In summary, in order to increase the sensitivity of this spectrometer (i.e. the minimum number of spins detectable in one second), the following measures are recommended according to the invention:

The use of a microwave amplifier 302 at the quantum limit to amplify the spin-echo signal. This increases by a factor of 10 to 50 the signal-to-noise ratio, and therefore the sensitivity of the spectrometer, i.e. the minimum number of detectable spins. At a temperature of 10 mK (temperature reached in commercially available dilution cryostats), the achieved sensitivity is estimated to be $10^3$ spins in a single echo, this representing an improvement of four orders of magnitude with respect to the best published performance.

In this case, sensitivity is further improved by illuminating the spectrometer with a squeezed vacuum, generated by a parametric amplifier 306 located before the input of the spectrometer. The squeezed vacuum decreases the noise on one of the quadratures of the microwave signal. By choosing the phase of this squeezed vacuum so that it coincides with the phase of the spin echo, the signal-to-noise ratio will be further increased by a factor that may be as high as 10.

Lastly, to even more greatly increase sensitivity, for samples 201 of very small size (of about 100 nm or 200 nm or less), it is possible to introduce a constriction 220 within the resonator 202, as close as possible to the sample 201. It is thus possible to achieve a sensitivity corresponding to the detection of a single spin in less than one second of acquisition time.

The invention claimed is:
1. A very-high-sensitivity spin-resonance spectroscopy device for detecting and characterizing electron spins in a given sample, comprising an electromagnetic microresonator having a resonant frequency ωr in the microwave domain and a quality factor Q and into which the sample is inserted, a device for creating a magnetic field B0 in the sample in order to bring into resonance with the resonant frequency ωr a transition frequency ωs of the spins, such that ωs=γB0, where γ is a gyromagnetic ratio of the spins, and a spin-detecting device receiving signals from the electromagnetic microresonator that is associated with the sample and comprising at least one low-noise amplifier operating at a temperature between 1 and 10 K, and a series of amplifiers and a demodulator operating at room temperature, wherein the electromagnetic microresonator is made of superconductive metal and is produced on the nanoscale in that it comprises an active zone consisting of an essentially parallelepipedal constriction with a thickness comprised between 8 and 30 nm, a width comprised between 10 and 500 nm and a length comprised between 100 and 5000 nm.

2. The device as claimed in claim 1, wherein the microresonator is made of niobium, aluminum, NbN, NbTiN, or TiN.

3. The device as claimed in claim 1, further comprising a Josephson parametric amplifier that is placed upstream of said low-noise amplifier and that operates at temperatures T respecting $T \leq \hbar \omega r / \kappa_B$ where $\hbar$ is a reduced Planck's constant and $\kappa_B$ is Boltzmann's constant.

4. The device as claimed in claim 3, further comprising an additional Josephson parametric amplifier operating at temperatures $T \leq \hbar \omega r / \kappa_B$ and placed such that an output of the additional Josephson parametric amplifier is connected to an input of said microresonator in order to produce a squeezed vacuum.

5. The device as claimed in claim 1, wherein the spin-detecting device is a continuous-wave device and comprises a device for injecting a microwave signal at the frequency ωr into the electromagnetic microresonator.

6. The device as claimed in claim 1, wherein the spin-detecting device is a pulsed-wave device and comprises a device for injecting sequences of brief pulses of microwave frequency equal to the frequency ωr into the electromagnetic microresonator in order to cause the spin to rotate by a well-defined Rabi angle.

7. A very-high-sensitivity spin-resonance spectroscopy method for detecting and characterizing electron spins in a given sample, comprising producing an electromagnetic microresonator having a resonant frequency ωr in the microwave domain and a quality factor Q and into which the sample is inserted; creating a magnetic field B0 in the sample in order to bring into resonance with the resonant frequency ωr a transition frequency ωs of the spins, such that ωs=γB0, where γ is a gyromagnetic ratio of the spins; and receiving signals from the electromagnetic microresonator with which the sample is associated via at least one low-noise amplifier operating at a temperature between 1 and 10 K, and a series of amplifiers and a demodulator operating at room temperature, wherein in the step of producing the electromagnetic microresonator an electromagnetic microresonator made of superconductive metal is chosen, which microresonator is produced on the nanoscale in that it comprises an active zone consisting of an essentially parallelepipedal constriction the dimensions of which are: a thickness of 8 to 30 nm, a width of 10 to 500 nm, and a length comprised between 100 and 5000 nm.

8. The method as claimed in claim 7, wherein, in the receiving signals from the electromagnetic microresonator step, a Josephson parametric amplifier is furthermore placed upstream of said low-noise amplifier said Josephson parametric amplifier operating at temperatures T respecting $T \leq \hbar \omega r / \kappa_B$ where $\hbar$ is a reduced Planck's constant and $\kappa_B$ is Boltzmann's constant.

9. The method as claimed in claim 8, wherein, in the step of producing an electromagnetic microresonator, an additional Josephson parametric amplifier operating at temperatures T respecting $T \leq \hbar \omega r / \kappa_B$ is placed such that an output of the additional Josephson amplifier is connected to an input of said microresonator in order to produce a squeezed vacuum.

10. The method as claimed in claim 8, wherein the measurement frequencies are comprised between 5 and 10 GHz and the temperature T is comprised between 10 and 200 mK.

11. The method as claimed in claim 8, wherein the measurement frequencies are comprised between 20 and 40 GHz and the temperature T is comprised between 1 and 3 K.

12. The device of claim 4, wherein the squeezed vacuum is a quantum state of the electromagnetic field in which noise in one of two quadratures is decreased with respect to vacuum quantum noise.

13. The method of claim 9, wherein the squeezed vacuum is a quantum state of the electromagnetic field in which noise in one of two quadratures is decreased with respect to vacuum quantum noise.

14. The device as claimed in claim 2, further comprising a Josephson parametric amplifier that is placed upstream of said low-noise amplifier and that operates at temperatures T respecting $T \leq \hbar \omega r / \kappa_B$ where $\hbar$ is a reduced Planck's constant and $\kappa_B$ is Boltzmann's constant.

15. The device as claimed in claim 2, wherein the spin-detecting device is a continuous-wave device and comprises a device for injecting a microwave signal at the frequency ωr into the electromagnetic microresonator.

16. The device as claimed in claim 3, wherein the spin-detecting device is a continuous-wave device and comprises a device for injecting a microwave signal at the frequency ωr into the electromagnetic microresonator.

17. The device as claimed in claim 2, wherein the spin-detecting device is a pulsed-wave device and comprises a device for injecting sequences of brief pulses of microwave frequency equal to the frequency ωr into the electromagnetic microresonator in order to cause the spin to rotate by a well-defined Rabi angle.

18. The device as claimed in claim 3, wherein the spin-detecting device is a pulsed-wave device and comprises a device for injecting sequences of brief pulses of microwave frequency equal to the frequency or ωr into the electromagnetic microresonator in order to cause the spin to rotate by a well-defined Rabi angle.

19. The method as claimed in claim 9, wherein the measurement frequencies are comprised between 5 and 10 GHz and the temperature T is comprised between 10 and 200 mK.

20. The method as claimed in claim 9, wherein the measurement frequencies are comprised between 20 and 40 GHz and the temperature T is comprised between 1 and 3 K.

* * * * *

UNITED STATES PATENT AND TRADEMARK OFFICE
CERTIFICATE OF CORRECTION

PATENT NO. : 10,422,838 B2
APPLICATION NO. : 15/554493
DATED : September 24, 2019
INVENTOR(S) : Patrice Bertet et al.

Page 1 of 1

It is certified that error appears in the above-identified patent and that said Letters Patent is hereby corrected as shown below:

In the Specification

Column 1, Line 9, delete "2013," and insert -- 2016, --.

In the Claims

Column 10, Line 6, Claim 8, delete "amplifier" and insert -- amplifier, --.

Column 10, Line 54, Claim 18, after "frequency" delete "or".

Signed and Sealed this
Seventh Day of January, 2020

Andrei Iancu
*Director of the United States Patent and Trademark Office*